(12) United States Patent
Harder

(10) Patent No.: US 6,762,338 B2
(45) Date of Patent: *Jul. 13, 2004

(54) COMPRESSION BANDAGE WITH TIGHTENING MEANS

(76) Inventor: Robert H. Harder, 8402 Oyster Cove, P.O. Box 189, Bena, VA (US) 23018

( * ) Notice: Subject to any disclaimer, the term of this patent is extended or adjusted under 35 U.S.C. 154(b) by 0 days.

This patent is subject to a terminal disclaimer.

(21) Appl. No.: 10/425,670

(22) Filed: Apr. 30, 2003

(65) Prior Publication Data

US 2003/0199801 A1 Oct. 23, 2003

Related U.S. Application Data

(63) Continuation of application No. 09/708,332, filed on Nov. 9, 2000, now Pat. No. 6,593,508.

(51) Int. Cl.[7] ................................................ A61F 13/00
(52) U.S. Cl. ......................... 602/56; 602/53; 606/203
(58) Field of Search ....................... 602/41–43, 53–56, 602/75, 78, 900; 606/203; 128/DIG. 15

(56) References Cited

U.S. PATENT DOCUMENTS

| | | | | |
|---|---|---|---|---|
| 3,255,749 A | * | 6/1966 | Smithers | 602/60 |
| 4,085,746 A | * | 4/1978 | Castiglia | 128/DIG. 15 |
| D250,277 S | * | 11/1978 | Takano | D24/189 |
| 4,205,674 A | * | 6/1980 | Porat et al. | 602/58 |
| 4,273,130 A | * | 6/1981 | Simpson | 606/203 |
| 4,926,848 A | * | 5/1990 | Shimkus et al. | 602/75 |
| 5,628,723 A | * | 5/1997 | Grau | 602/53 |
| 6,152,893 A | * | 11/2000 | Pigg et al. | 602/75 |
| 6,593,508 B1 | * | 7/2003 | Harder | 602/56 |

\* cited by examiner

Primary Examiner—Nicholas D. Lucchesi
Assistant Examiner—Quang D Thanh
(74) Attorney, Agent, or Firm—Nixon & Vanderhye P.C.

(57) ABSTRACT

Disclosed is a strip of bandaging material having Velcro® strips at either end on opposite sides of the material. An absorbent pad is fixed near one end and on the side opposite the Velcro® strip. On the side opposite the absorbent pad, an S hook is provided with one end fastened to the material and the other end free. The absorbent pad is located over the wound and the longer end of material is wound around the extremity and fixed in place with the Velcro® stripe at the near end of the material. The remaining material is passed through the hook and pulled back in order to apply pressure to the wound and reduce blood loss. The remainder of the material is wrapped around the extremity and secured in place with the Velcro® strip on the far end.

2 Claims, 3 Drawing Sheets

COMPRESSION BANDAGE WITH TIGHTENING MEANS

This application is a Continuation of application Ser. No. 09/708,332, filed Nov. 9, 2000, now U.S. Pat. No. 6,593,508 the entire content of which is hereby incorporated by reference.

BACKGROUND OF THE INVENTION

1. Field of the Invention

The current compression bandages that are employed to give first aid to trauma wounds are awkward and difficult to adequately tighten securely over the wound. For traumas that are aggressively bleeding, this tightening is necessary.

2. Discussion of Prior Art

Past tightening devices that are attached to trauma bandages do not allow a large force to be placed on the tightening device. In addition, the past bandages needed hand tied knots to fasten the bandage to the wound, resulting in loosening of the bandage on the trauma.

SUMMARY OF THE INVENTION

The compression bandage with tightening means is based on the use of a elastic bandage roll that has a absorbent pad attached near one end, each end of the elastic roll having male Velcro® strips (the trademark for one type of hook and loop fastener system having the male or micro-hook characteristics) to allow closure, in the initial and final application, and a metal hook attached through the elastic roll and absorbent pad attached thereto. The application of the absorbent pad to a trauma seals that wound, the initial Velcro® strip allowing placement of the pad on the wound. The elastic roll, after wrapping once around the extremity, is engaged into the hook sewn into the elastic bandage and absorbent pad. The elastic bandage is then pulled against the hook to give compression to the pad and the wound. The elastic strip is then stretched and wound around the wound, with the Velcro® strip at the end used to finish fasten. This invention allows an individual to place a bandage on a wound and, with one hand if necessary, put a high degree of compression on the wound, easily fastening and securing.

BRIEF DESCRIPTION OF THE DRAWINGS

A better understanding of the invention will be had by reference to the following drawings in which.

DETAILED DISCUSSION OF EMBODIMENTS

The present invention, an elastic bandage, comprises a strip of material 10 in the form of a roll, at least 3" to 6" in width, and 48" to 60" long. At each end of the material male Velcro® strips 12, 14 are fastened. Near one end of the elastic roll (the ends of the material are defined as the near end and the far end), a high absorbent pad 16, at least 5"×8" is attached. In one embodiment, at the center of the pad, but on the opposite side of the material from the absorbent pad 16, an anchoring point, in a preferred embodiment, an S hook 18 is attached, the base of the S hook attached, the top being free.

Figure 1:
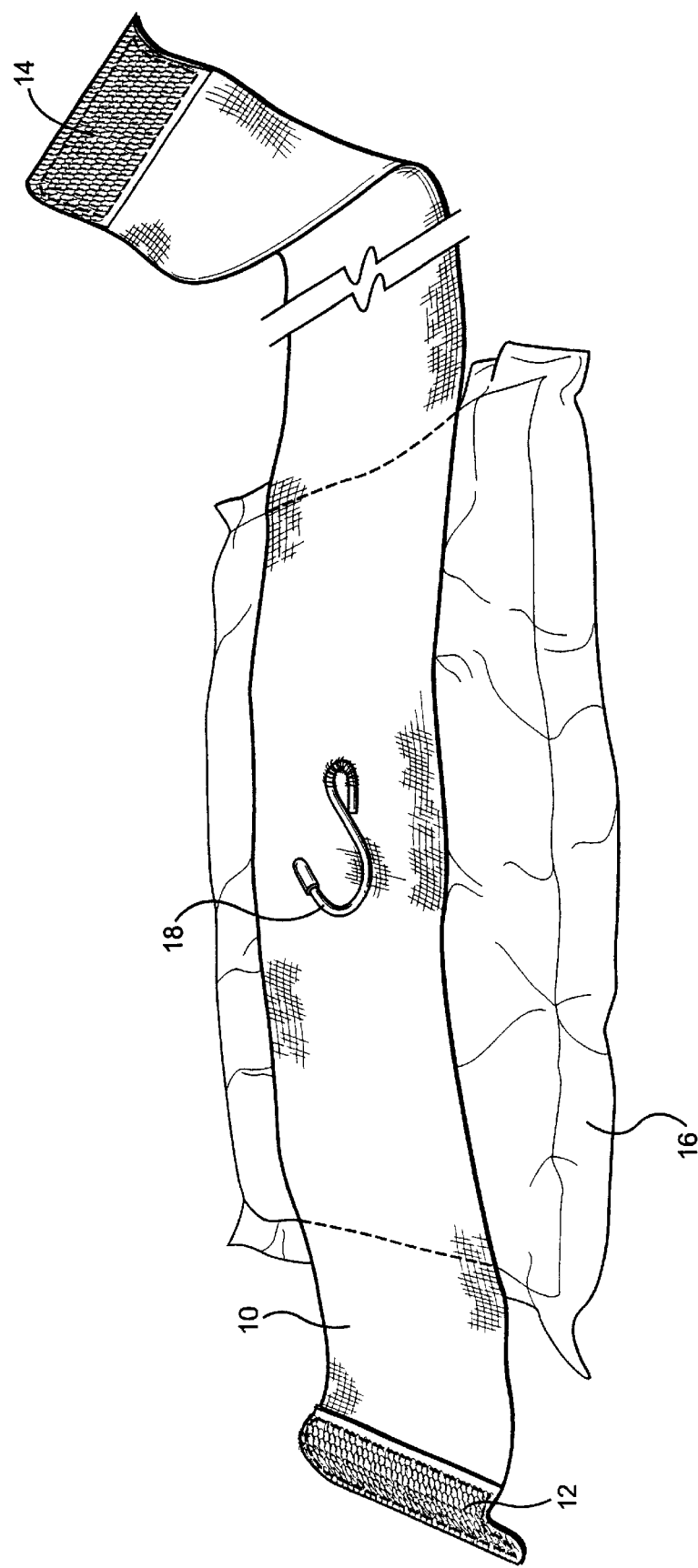
FIG. 1 is a perspective view of the compression bandage of the present invention.
Figure 2:
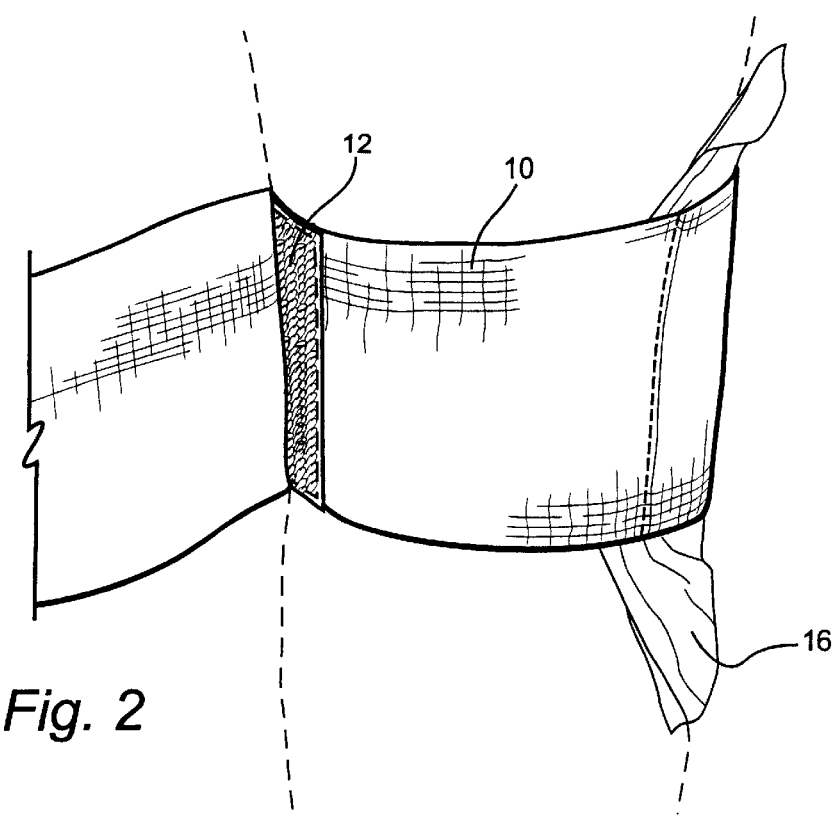
FIG. 2 is a perspective view showing the initial step of fixing the absorbent pad on the bandage into position over the wound.
Figure 3:
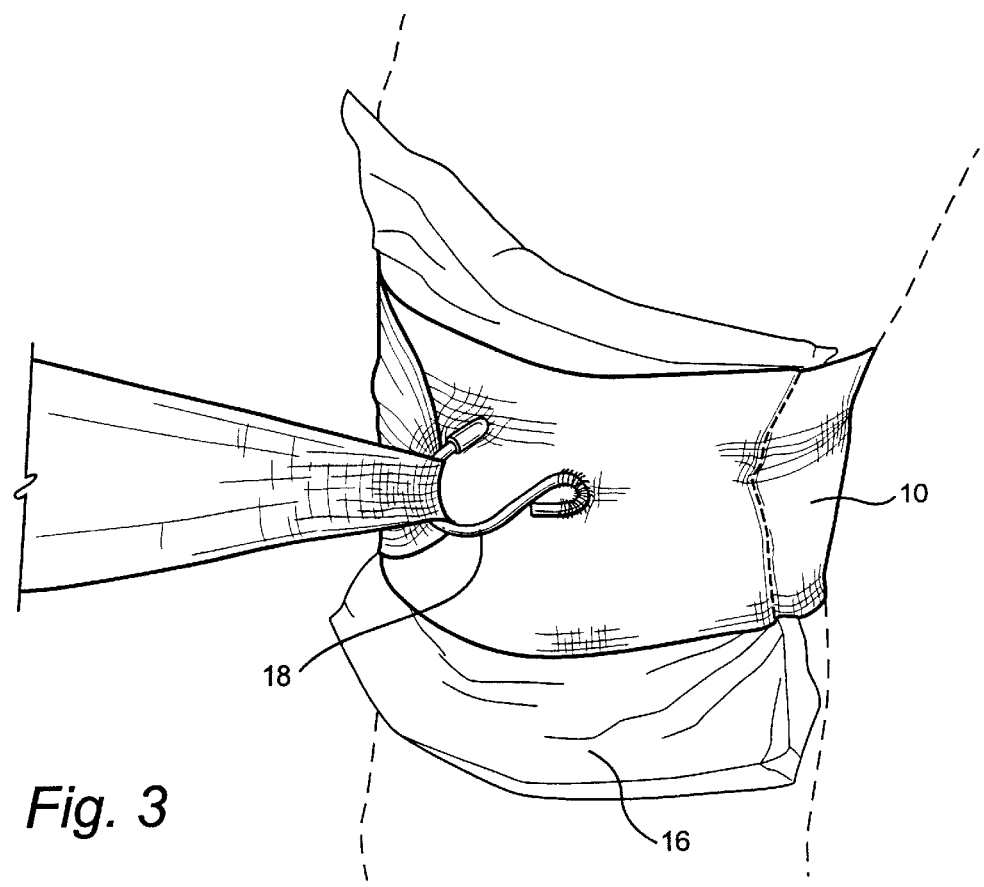
FIG. 3 is a perspective view showing the second step of passing the remainder of the bandage through the compression "S" hook and applying tension to the bandage.
Figure 4:
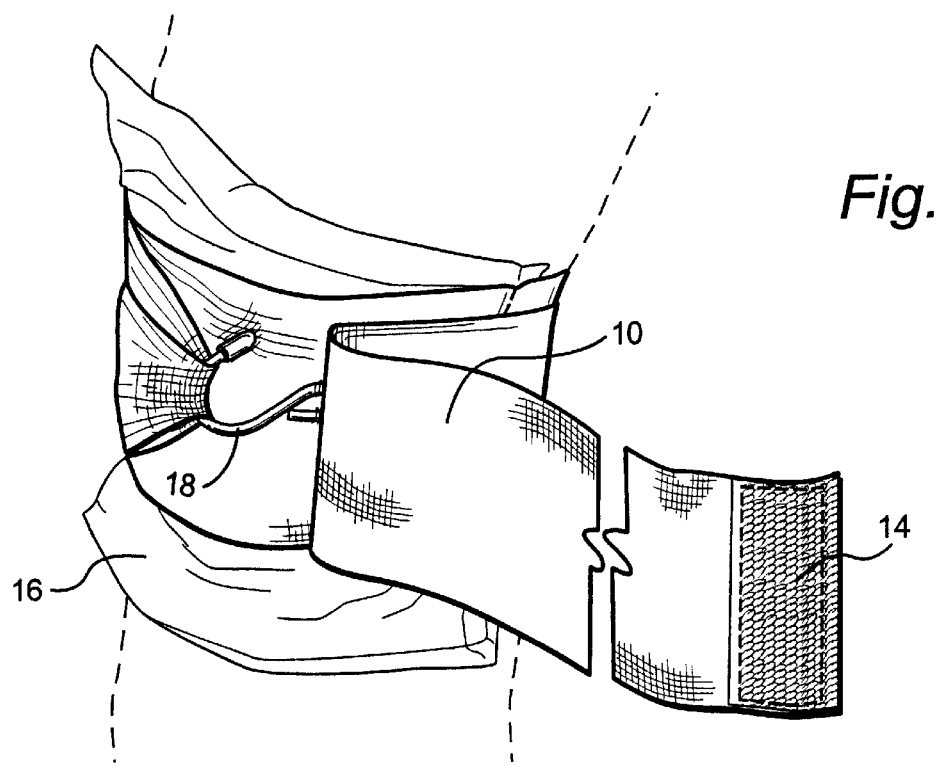
FIG. 4 is a perspective view showing the third step of winding the remainder of the bandage around the wound thereby applying additional pressure to the wound.
Figure 5:
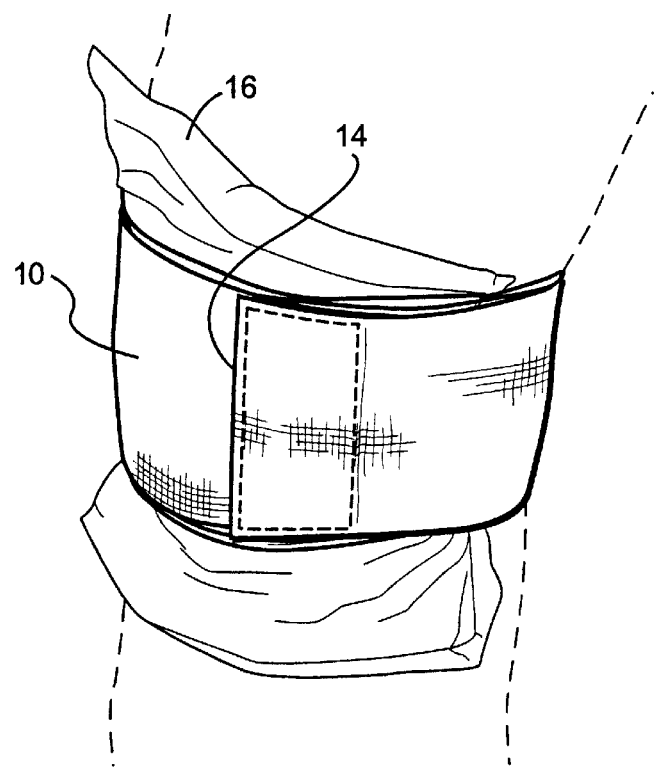
FIG. 5 is a perspective view showing the final step of completing the wrapping of the bandage and removably fixing the free end of the bandage in place.

After the pad 16 is located over the wound, the elastic roll is wrapped once around, and the roll is engaged into the free end of the S hook and tightened over the trauma by pulling on the elastic in the opposite direction of the initial wrap. The use of the Velcro® strips allows ease of situating the pad and closure. The Velcro® strip 12 located at the near end of the material is located on the same side of the material as the S hook 18 and initially secures the bandage as the material is initially wrapped around the extremity, with the hooks in the male Velcro® strip engaging the material to temporarily hold the bandage in place as shown in FIG. 2. The material is then passed through the S hook 18 as shown in FIG. 3 and pulled to provide increased tension in the material, thereby tightening the bandage over the wound and at the same time acting as a tourniquet to reduce blood loss. The remaining material is wound over the wound as shown in FIG. 4 and secured in place by engaging the Velcro® strip on the far end of the material with the material itself. Note that in order for the near end Velcro® stripe 12 to engage the material 10 as shown in FIG. 2 it has to be located on the same side of the material 10 as the S hook 18 whereas the far end Velcro® strip 14 in order to engage the material must be located on the same side of the material 10 as the absorbent pad 16.

What is claimed is:

1. An easily applied and secured compression bandage, said bandage comprising:

a bandage comprising a strip of material having first and second sides, said material having relatively near and far ends;

a pad, said pad attached to the first side of said material closer to said near one of said ends;

an anchoring point, attached to the second side of said material, for reversing the direction of wrap of said other end of said material; and a first strip of micro-hooks located on said second side at said near end of said material, said micro-hooks comprising a portion of a hook and loop fastener system, said material comprises a material having loops releasably engageable with said micro-hooks, wherein, when applied, the pad is positioned over a wound on a body or body part, and the far end of said material is passed around the body or body part in one direction of wrap, the material passing over said first strip is fastened thereto temporarily maintaining the position of the pad over the wound, is passed through the anchoring point and its direction of wrap reversed, is pulled sufficiently tight to deter bleeding and is wound around and fixed to the bandage, wherein said anchoring point comprises an S hook having a base and a top, said base attached on said other side of said material adjacent said pad and said top being free.

2. An easily applied and secured compression bandage, said bandage comprising:

a bandage comprising a strip of material having first and second sides, said material having relatively near and far ends;

a pad, said pad attached to the first side of said material closer to said near one of said ends;

an anchoring point, attached to the second side of said material, for reversing the direction of wrap of said other end of said material; and a first strip of micro-hooks located on said second side at said near end of said material, said micro-hooks comprising a portion of a hook and loop fastener system, said material comprises a material having loops releasably engageable with said micro-hooks, wherein, when applied, the pad is positioned over a wound on a body or body part, and the far end of said material is passed around the body or body part in one direction of wrap, the material passing over said first strip is fastened thereto temporarily maintaining the position of the pad over the wound, is passed through the anchoring point and its direction of wrap reversed, is pulled sufficiently tight to deter bleeding and is wound around and fixed to the bandage, wherein said anchoring point comprises an S hook having a base and a top, said base attached on said other side of said material adjacent said pad and said top being free, wherein said S hook is metal.

* * * * *